United States Patent [19]

Schach et al.

[11] Patent Number: 5,492,875
[45] Date of Patent: Feb. 20, 1996

[54] CATALYST FOR NUCLEOPHILIC AROMATIC SUBSTITUTIONS

[75] Inventors: Thomas Schach, Gernsheim; Theodor Papenfuhs, Frankfurt am Main, both of Germany

[73] Assignee: Hoechst AG, Germany

[21] Appl. No.: 277,480

[22] Filed: Jul. 19, 1994

[30] Foreign Application Priority Data

Jul. 21, 1993 [DE] Germany .......................... 43 24 366.5

[51] Int. Cl.$^6$ ...................................... B01J 31/00
[52] U.S. Cl. ........................ 502/164; 502/150; 502/162; 502/200; 502/208
[58] Field of Search .................................. 502/150, 162, 502/164, 167, 200, 208

[56] References Cited

U.S. PATENT DOCUMENTS

| | | | |
|---|---|---|---|
| 3,123,641 | 3/1964 | Longley | 260/567.6 |
| 3,141,905 | 7/1964 | Longley | 260/567.6 |
| 4,069,262 | 1/1978 | Kunz | 260/646 |
| 4,140,719 | 2/1979 | Tull et al. | 260/580 |
| 4,287,374 | 9/1981 | North . | |
| 4,694,104 | 9/1987 | Chakrabarti et al. | 564/285 |

FOREIGN PATENT DOCUMENTS

| | | |
|---|---|---|
| 0423676A3 | 1/1993 | European Pat. Off. . |
| WO87/04149 | 7/1987 | WIPO . |
| WO-A 9200270 | 9/1992 | WIPO . |

*Primary Examiner*—Sharon Gibson
*Attorney, Agent, or Firm*—Connolly & Hutz

[57] ABSTRACT

A catalyst consisting essentially of a quaternary ammonium compound, comprising at least one linear or branched alkoxypolyoxyalkyl chain, and a quaternary ammonium or phosphonium salt or a polyether, or a mixture of each of the specified compounds, is suitable for accelerating, or making possible for the first time, many nucleophilic aromatic substitutions.

10 Claims, No Drawings

CATALYST FOR NUCLEOPHILIC AROMATIC SUBSTITUTIONS

The invention relates to a novel catalyst system by means of which many nucleophilic substitutions on aromatics are accelerated or made possible for the first time.

Nucleophilic substitutions play an important role in the synthesis of substituted aromatics. To carry out these reactions, comparatively high reaction temperatures are required, often between 200° and 320° C., which sometimes gives considerable amounts of decomposition products. In general a solvent cannot be omitted, so that the space-time yields are significantly lower than in solvent-free processes.

As alternatives, use can be made of conventional phase transfer catalysts which enable some of the above-described disadvantages to be improved. Other problems such as, for example, poor stirrability of the reaction suspension in solvent-free processes remain. The phase transfer catalysts hitherto used have been quaternary alkylammonium or alkylphosphonium salts (U.S. Pat. No. 4,287,374), pyridinium salts (WO 87/04149) or crown ethers, some of which show only low reactivities or are only moderately stable at the reaction temperatures required.

In view of these limitations and disadvantages, there was a great need for an improved catalyst system by means of which the inherent disadvantages of the known processes are avoided and good to very good yields, lower reaction temperatures and shortened reaction times are made possible and smaller amounts of polymeric decomposition products are obtained. Particular importance has been attached to, in particular, coping with stirring problems and work-up problems in solvent-free processes and in processes using only very small amounts of solvent.

It has been found that a mixture of a quaternary ammonium compound comprising at least one alkoxypolyoxyalkyl radical, a quaternary ammonium or phosphonium salt and/or a polyether suprisingly meets the abovementioned requirements.

The present invention provides a catalyst for nucleophilic substitutions, consisting essentially of a mixture of a) one or more quaternary ammonium compound(s) of the formula (1)

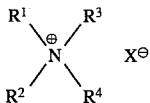
(1)

in which $R^1$, $R^2$ and $R^3$ are identical or different and are a linear or branched alkoxypolyoxyalkyl radical of the formula $-(C_mH_{2m}O)_pR^5$, in which $R^5$ is hydrogen or a linear or branched alkyl radical having from 1 to 16, preferably from 1 to 8, carbon atoms, m is an integer from 1 to 10, preferably from 1 to 5, and p is a number from 1 to 15, preferably from 2 to 10;

or a linear or branched alkyl radical having from 1 to 30, preferably from 1 to 18 carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;

$R^4$ is a linear or branched alkoxypolyoxyalkyl radical of the formula $-(C_mH_{2m}O)_pR^5$ and;

$X^-$ is an inorganic anion, preferably fluoride, chloride, bromide, $SO_4^{2-}/2$ or hydrogen sulfate;

and b) one or more quaternary ammonium salt(s) or phosphonium salt(s) of the formula (2)

(2)

in which $R^6$, $R^7$, $R^8$ and $R^9$ are identical or different and are a linear or branched alkyl radical having 1 to 22, preferably from i to 16, carbon atoms; or an unsubstituted or substituted aryl radical or a $C_1$–$C_4$-alkyl aryl radical, with aryl being phenyl or naphthyl and the said substituents being halogen, $C_1$–$C_4$-alkyl, $C_1$–$C_4$-alkoxy, nitro or cyano; and Y is N or P;

or of a mixture of one or more compound(s) of the formula (1)

and c) one or more polyether(s) of the formula (3)

(3), in which $R^{10}$ and $R^{11}$ are identical or different and are hydrogen or a linear or branched alkyl radical having from 1 to 16, preferably from 1 to 8, carbon atoms;

x is an integer from 2 to 6, preferably 2 or 3, and r is a number from 0 to 20, preferably from 4 to 14;

or a crown ether;

or of a mixture of the compounds specified in a), b) and c).

In the compounds of the formula (1) and (2) the anion $X^-$ can in each case be identical or different.

The mixing ratios of the components a) and b), a) and c), and also a), b) and c) can vary within a wide range, with the proviso that the component a) makes up from 5 to 95% by weight, preferably from 20 to 80% by weight, of the total catalyst.

In the linear or branched alkoxypolyoxyalkyl radical of the formula $-(C_mH_{2m}O)_pR^5$ present in the compound of the formula (1), identical or different alkoxy units can be linked to one another. The number of linear or branched alkoxypolyoxyalkyl radicals present in the compound of the formula (1) is preferably 1 or 2. For the purposes of the present invention, particularly preferred compounds of the formula (1) are dimethyldi(ethoxypolyoxypropyl)ammonium chloride, dimethyldi(ethoxypolyoxypropyl methyl ether)ammonium chloride, dimethyl(ethoxypolyoxypropyl)(ethoxypolyoxypropyl methyl ether)ammonium chloride, dimethyldi(ethoxypolyoxyethyl)ammonium chloride, dimethyldi(ethoxypolyoxyethyl methyl ether) ammonium chloride, dimethyl(ethoxypolyoxyethyl) (ethoxypolyoxyethyl methyl ether)ammonium chloride, each having a mean chain length p of 3, furthermore trimethyl(ethoxypolyoxypropyl)ammonium chloride and trimethyl(ethoxypolyoxypropyl methyl ether)ammonium chloride, each having a mean chain length p of 8, or a mixture of the specified compounds.

The described compounds of the formula (1) can be prepared in a known manner (U.S. Pat. No. 3,123,641; U.S. Pat. No. 3,141,905) from the corresponding ethanolamines which, after reaction with alkylene oxides and subsequent quaternization with or without simultaneous etherification, give the desired compounds in good yields.

For the purposes of the present invention, preferred compounds of the formula (2) are octadecyl-trimethylammonium chloride, distearyldimethylammonium chloride, tetramethylammonium chloride, tetramethyl-ammonium bromide, hexadecyltrimethylammoniumchloride, benzyltrimethylammonium chloride, hexadecyltributyl-phosphonium bromide, stearyltributylphosphoniumbromide, tetrabutylphosphonium chloride, tetrabutylphosphonium bromide and tetraoctylphosphoniumbromide.

For the purposes of the present invention, preferred polyethers of the formula (3) possess a mean molecular mass between 300 and 800. Particular preference is given to a mixture of polyethylene glycol dimethyl ethers having chain lengths r of from 6 to 17 and a mean molecular mass of 500. In place of or in combination with polyethers of the formula (3), crown ethers, for example 18-crown-6, can also be used.

Suitable starting compounds for the nucleophilic aromatic substitution catalyzed according to the invention are aromatics of the benzene, naphthalene and pyridine types comprising at least one of the leaving groups $F^-$, $Cl^-$, $Br^-$, $I^-$, $NO_2^-$ or $SO_3^-$ and at least one electron-acceptor group selected from the group consisting of $-CF_3$, $-CCl_3$, $-CN$, $-NO_2$, $-COOH$, $-COCl$, $-SO_2Cl$, $-COBr$, $SO_2Br$, $-COF$, $-SO_2F$, $SO_3H$ or $-SO_3$-alkyl. Multiply halogenated aromatics can also be reacted without an electron-acceptor group. The said aromatics can also have further substituents, for example alkyl radicals, amino groups, hydroxy groups or alkoxy groups.

The nucleophiles used for the nucleophilic aromatic substitution catalyzed according to the invention are fluorides, cyanides, hydroxides, alkoxides or amine salts of alkali metals or monovalent transition metals. To introduce the CN group, CuCN is particularly suitable. To introduce phenoxide, SH, SR or amine groups, the respective phenols, mercaptans or amines are themselves often sufficient, so that the use of the corresponding metal salt can be omitted.

In the nucleophilic aromatic substitution, the catalyst of the invention is advantageously used in amounts from 1 to 35% by weight, preferably from 5 to 25% by weight, based on the aromatic starting compound. The molar ratio of catalyst to the aromatic is here equal to or less than 1:8, preferably from 1:25 to 1:100.

As regards the molar ratio of the starting compound to the nucleophile, use is advantageously made of from 1.0 to 2.5 mol of nucleophile per mol of aromatic. In cases in which an excess of nucleophile leads to secondary reactions, a deficiency of the nucleophile can also be used. The catalyst of the invention is generally suitable for nucleophilic aromatic substitutions, but particularly for chlorine-fluorine exchange reactions to prepare fluoroaromatics, for halogen-alkoxy exchange reactions or for bromine-cyanide exchange reactions.

Multiple exchange reactions without solvent have hitherto been possible only with limitations. The high salt content of the reaction suspension generally led to non-stirrable systems which led to only small conversions and yields, even under the most favorable conditions. The use of the catalyst of the invention now gives no stirring problems, even at very high salt contents in the reaction suspension, so that even double exchange reactions can usually be carried out without problems in the absence of solvent.

Surprisingly, the use of the catalyst of the invention reduces the viscosity of the reaction suspension. Finally, the simultaneously significantly lower reaction temperatures compared with the prior art, together with the good stirrability of the reaction suspension, to a significant increase in the yield and a reduction of secondary reactions. While temperatures of from 200° C. to over 300° C. have hitherto been required for nucleophilic aromatic substitutions, the reaction temperatures using the catalyst of the invention are from 20° to 200° C.

The catalyst of the invention can be used in the presence or absence of solvents. If solvents are used, aprotic and dipolar aprotic and also protic solvents are suitable. Suitable dipolar aprotic solvents are, for example, dimethyl sulfoxide, dimethyl sulfone, sulfolane, dimethylformamide, dimetlhyl acetamide, 1,3-dimethylimidazolin-2-one, acetonitrile and benzonitrile. Suitable aprotic solvents without pronounced dipolar character are, for example, benzene, toluene, xylene, chlorotoluenes, chlorobenzene and dichlorobenzenes. The use of aprotic solvents such as, for example, alcohols is likewise possible. The aprotic solvents used are methanol, ethanol, propanol, butanol, i-propanol or polyalkylene glycols having ethylene, propylene, or butylene units.

The aprotic or dipolar aprotic solvent can be used in any amounts, however, preference is given to using small amounts in the range from 5 to 30% by weight based on the aromatic used. When using protic solvents, the amounts used are in the range from 0.1 to 5% by weight, preferably from 0.1 to 2% by weight, based on the aromatic used.

The catalyst of the invention can be used at atmospheric pressure and also at superatmospheric or subatmospheric pressure. This property is utilized, for example, by adding small amounts of a low-boiling aprotic solvent which forms an azeotrope with water, such as, for example, benzene, xylene, mesitylene or toluene, to the reaction suspension prior to the start of the reaction. Subsequently, part of the solvent is again removed, together with water, from the reaction suspension by application of a vacuum. This process procedure allows the reaction rate and the yield to be increased and the formation of byproducts to be minimized.

The catalyst of the invention can be used in the presence or absence of atmospheric oxygen; preference is given to working under protective gas such as, for example, argon or nitrogen.

When using the catalyst of the invention, it must be ensured that the reaction mixture is well mixed during the whole reaction.

The products which can be produced by nucleophilic aromatic substitution play an important role as intermediates in the field of crop protection and as synthetic building blocks for pharmaceuticals and dyes.

The following examples illustrate the catalyst of the invention, without limiting it to them. For the purposes of the present invention, "polyethylene glycol dimethyl ethers 500" is the said polyether having a mean molecular mass of about 500. The trimethyl(ethoxypolyoxypropyl)ammonium chloride used in the examples has a mean chain length p of 8 and was used as product having a purity of from 84 to 89% by weight. This product additionally contains from 10 to 13% by weight of free polypropylene glycol and up to 2% by weight of water.

The dimethyldi(ethoxypolyoxypropyl)ammonium chloride used has a mean chain length p of 3 and is a product having a purity of from 90 to 95% by weight, which additionally contains from 5 to 10% by weight of polypropylene glycol and about 0.2% by weight of water.

If the two catalysts were used as etherified compounds, the polypropylene glycols were likewise in etherified form. In the case of dimethoxydi(ethoxy-polyoxypropyl methyl ether) ammonium chloride the degree of etherification was 86%.

The course of the reaction over time was followed by gas chromatographic analysis (GC) and the amount of the desired product present in the reaction mixture in each case was given in the form of GC percentage areas.

EXAMPLE 1

2,4-difluoronitrobenzene

In a 500 ml flange flask and fitted with a distillation bridge and impeller stirrer, 72.0 g (1.24 mol) of potassium fluoride, 14.0 g (0.027 mol) of dimethyldi (ethoxypolyoxypropyl) ammonium chloride and 7.0 g (0.014 mol) of polyethylene glycol dimethyl ether 500 were introduced at 100° C. into the melt of 120 g (0.62 mol) of 2,4-dichloronitrobenzene. The temperature was raised to 120° C. and the reaction suspension was stirred for 28 hours at this temperature. Amount of 2,4-difluoronitrobenzene formed: after 6 hours: 11 GC area-%. after 28 hours: 56 GC area-%.

EXAMPLE 2

2-fluoronitrobenzene

In a 2 liter flange flask and fitted with a distillation bridge and impeller stirrer, 290.5 g (5.0 mol) of potassium fluoride, 71.1 g (0.1 mol) of trimethyl(ethoxypolyoxypropyl)ammonium chloride, 11.0 g (0.1 mol) of tetramethylammonium chloride and 17.7 g (0.035 mol) of polyethylene glycol dimethyl ether 500 were introduced at 120° C. into the melt of 630 g (4.0 mol) of 2-chloronitrobenzene. Subsequently, the mixture was azeotropically dried using 100 g (0.94 mol) of xylene and the reaction mixture was stirred for 28 hours at a temperature of 150° C. Amount of 2-fluoronitrobenzene formed: after 6 hours: 36 GC area-%. after 28 hours: 74 GC area-%.

EXAMPLE 3

2,3,4-trifluoronitrobenzene

In a 1.5 liter flange flask and fitted with a distillation bridge and anchor stirrer, 488 g (8.4 mol) of potassium fluoride and 40.0 g (0.07 mol) of dimethyldi(ethoxypolyoxypropyl methyl ether)ammonium chloride, 20.0 g (0.04 mol) of polyethylene glycol dimethyl ether 500 and 20.4 g (0.06 mol) of tetrabutylphosphonium bromide were introduced at 110° C. into the melt of 840 g (4 mol) of 2,4-dichloro-3-fluoronitrobenzene. Subsequently, the mixture was azeotropically dried using 60 g (0.57 mol) of xylene and stirred for 21 hours at a temperature of 150° C. Amount of 2,3,4-trifluoronitrobenzene formed: after 5 hours: 13 GC area-%. after 21 hours: 65 GC area-%.

EXAMPLE 4

2,4-dichloro-5-fluorobenzonitrile 97.6 g (0.4 mol) of 5-bromo-2,4-dichlorofluorobenzene, 35.8 g (0.4 mol) of copper(I)cyanide, 10.0 g (0.014 mol) of trimethyl(ethoxypolyoxypropyl)ammonium chloride, 5.0 g (0.015 mol) of tetrabutylphosphonium bromide and 5.0 g (0.01 mol) of polyethylene glycol dimethyl ether 500 were introduced together with 20.0 g (0.19 mol) of xylene into a 250 ml 3-neck flask fitted with a reflux condenser and blade stirrer and azeotropically dried at up to 150° C. under reduced pressure. Amount of 2,4-dichloro-5-fluorobenzonitrile formed: after 5 hours: 19 GC area-%. after 26 hours: 75 GC area-%.

COMPARATIVE EXAMPLE 1

2,4-dichloro-5-fluorobenzonitrile 48.8g (0.2 mol) of 5-bromo-2,4-dichlorofluorobenzene and 17.9 g (0.2 mol) of copper(I) cyanide were introduced into a 100 ml 3-neck flask fitted with a reflux condenser and blade stirrer and stirred at 150° C. for 4 hours (no reaction). The reaction suspension was heated to 200° C. and stirred for a further 4 hours at this temperature: no reaction, 0 GC area-%.

EXAMPLE 5

3-chloro-2-fluoronitrobenzene

In a 1.5 liter flange flask and fitted with a distillation bridge and impeller stirrer, 279 g (4.8 tool) of fluoride, 218.5 g (0.3 mol) of trimethyl(ethoxypolyoxypropyl)ammonium chloride and 11.5 g (0.023 mol) of polyethylene glycol dimethyl ether 500 were introduced at 100° C. into the melt of 768 g (4 mol) of 2,3-dichloronitrobenzene. Subsequently, the mixture was azeotropically dried using 200 g (1.9 mol) of xylene and stirred for 24 hours at a temperature of 100° C. Amount of 3-chloro-2-fluoronitrobenzene formed: after 5 hours: 18 GC area-%. after 24 hours: 47 GC area-%.

COMPARATIVE EXAMPLE 2

3-chloro-2-fluoronitrobenzene 57.6 g (0.3 mol) of 2,3-dichloronitrobenzene and 13.9 g (0.24 mol) of potassium fluoride were introduced into a 100 ml flange flask and fitted with a reflux condenser and blade stirrer and stirred at 150° C. for 2 hours (no reaction). The reaction suspension was heated to 190° C. and stirred for a further 4 hours at this temperature. Amount of 3-chloro-2-fluoronitrobenzene formed: after 2 hours: 1 GC area-%. after 8 hours: 8 GC area-%.

EXAMPLE 6

4-fluorobenzonitrile

In a 250 ml flange flask and fitted with an impeller stirrer, 69.6 g (1.2 mol) of potassium fluoride, 6.9 g (0.02 mol) of tetrabutyl-phosphonium bromide, 13.8 g (0.02 mol) of dimethyldi(ethoxypolyoxypropyl)ammonium chloride, 13.8 g (0.028 mol) of polyethylene glycol dimethyl ether 500 and 20 g of xylene were metered at 120° C. into the melt of 137.6 g (1.0 mol) of 4-chlorobenzonitrile. After stirring for 30 minutes, the reaction suspension was azeotropically dried by distilling off the xylene under vacuum. The reaction suspension was stirred for 30 hours at 190° C. Amount of 4-fluorobenzonitrile formed: after 9 hours: 12 GC area-% after 30 hours: 48 GC area-%, besides 45 GC area-% of unreacted 4-chlorobenzonitrile.

EXAMPLE 7

5-chloro-2-nitrophenol 57.6 g (0.3 mol) of 2,4-dichloronitrobenzene were admixed with 10 g (0.014 mol) of dimethyldi(ethoxypolyoxypropyl)ammonium chloride and 150 ml of 20% by weight strength NaOH at 60° C. The two-phase reaction mixture was stirred for 21 hours at 100° C. and subsequently brought to pH 1 using HCl. Amount of 5-chloro-2-nitrophenol formed: after 21 hours: 40 GC area-%.

We claim:
1. A catalyst suitable for nucleophilic substitution, consisting essentially of:
a mixture of a component a) and a component b), wherein component a) is at least one quaternary ammonium compound of the formula (1)

in which
R$^1$, R$^2$ and R$^3$ are identical or different and are a linear or branched alkoxypolyoxyalkyl radical of the formula —$(C_mH_{2m}O)_pR^5$, in which R$^5$ is hydrogen or a linear or branched alkyl radical having from 1 to 16 carbon atoms, m is an integer from 1 to 10 and p is a number from 1 to 15; a linear or branched alkyl radical having from 1 to 30 carbon atoms; or an unsubstituted phenyl or naphthyl radical; or a substituted phenyl or naphthyl radical, with the substituents being halogen, C$_1$–C$_4$-alkyl, C$_1$–C$_4$-alkoxy, nitro or cyano;
R$^4$ is a linear or branched alkoxypolyoxyalkyl radical of the formula —$(C_mH_{2m}O)_pR^5$, wherein R$^5$, m, and p are as defined above, and;
X is an inorganic anion; and
component b) is at least one quaternary ammonium salt or at least one phosphonium salt of the formula (2)

in which
R$^6$, R$^7$, R$^8$, and R$^9$ are identical or different and are a linear or branched alkyl radical having 1 to 22 carbon atoms; or an unsubstituted or substituted aryl radical or a C$_1$–C$_4$-alkyl-aryl radical, with aryl being phenyl or napthyl, and the said substituents are halogen, C$_1$–C$_4$-alkyl, C$_1$–C$_4$-alkoxy, nitro or cyano; and
Y is N or P; or
the mixture consists essentially of component a) as defined above, and a component c), which is at least one polyether of the formula (3)

in which
R$^{10}$ and R$^{11}$ are identical or different and are hydrogen or a linear or branched alkyl radical having from 1 to 16 carbon atoms,
x is an integer from 2 to 6 and
r is a number from 0 to 20; or
the mixture consists essentially of component a) as defined above, and a crown ether; or
the mixture consists essentially of component a) as defined above, component b) as defined above, and component c) as defined above.
2. A catalyst as claimed in claim 1, wherein
R$^1$, R$^2$ and R$^3$ are identical or different and are a linear or branched alkoxypolyoxyalkyl radical of the formula —$(C_mH_{2m}O)_pR^5$ in which R$^5$ is hydrogen or a linear or branched alkyl radical having from 1 to 8 carbon atoms, m is an integer from 1 to 5 and p is a number from 2 to 10; or a linear or branched alkyl radical having from 1 to 18 carbon atoms; or an unsubstituted phenyl or naphthyl radical, or a substituted phenyl or naphthyl radical, with the substituents being halogen, C$_1$–C$_4$-alkyl, C$_1$–C$_4$-alkoxy, nitro or cyano;
R$^4$ is a linear or branched alkoxypolyoxyalkyl radical of the formula —$(C_mH_{2m}O)_pR^5$, in which R$^5$ is hydrogen or a linear or branched alkyl radical having from 1 to 8 carbon atoms, m is an integer from 1 to 5 and p is a number from 2 to 10; and
X$^-$ is fluoride, chloride, bromide, SO$_4^{2-}$/2 or hydrogen sulfate.
3. A catalyst as claimed in claim 1, wherein
R$^6$, R$^7$, R$^8$ and R$^9$ are identical or different and are a linear or branched alkyl radical having from 1 to 16 carbon atoms; or an unsubstituted or substituted aryl radical or a C$_1$–C$_4$-alkyl aryl radical, with aryl being phenyl or naphthyl and the said substituents being halogen, C$_1$–C$_4$-alkyl, C$_1$–C$_4$-alkoxy, nitro or cyano.
4. A catalyst as claimed in claim 1, wherein
R$^{10}$ and R$^{11}$ are identical or different and are hydrogen or a linear or branched alkyl radical having from 1 to 8 carbon atoms,
x is the integer 2 or 3 and
r is a number from 4 to 14.
5. A catalyst as claimed in claim 1 wherein the component a) makes up from 5 to 95% by weight of the total catalyst.
6. A catalyst as claimed in claim 1 wherein the component a) makes up from 20 to 80% of the total catalyst.
7. A catalyst as claimed in claim 1, wherein one or two alkoxypolyoxyalkyl radicals are present in the compound of the formula (1).
8. A catalyst as claimed in claim 1, wherein the compound of the formula (1) is dimethyldi(ethoxypolyoxypropyl)ammonium chloride, dimethyldi(ethoxypolyoxypropyl methyl ether)ammonium chloride, dimethyl(ethoxypolyoxypropyl) (ethoxypolyoxypropyl methyl ether)ammonium chloride, dimethyldi(ethoxypolyoxyethyl)ammonium chloride, dimethyldi(ethoxy-polyoxyethyl methyl ether)ammonium chloride, dimethyl-(ethoxypolyoxyethyl) (ethoxypolyoxyethyl methyl ether)ammonium chloride, each having a mean chain length p of 3, or trimethyl(ethoxypolyoxypropyl)ammonium chloride, or trimethyl(ethoxypolyoxypropyl methyl ether)ammonium chloride, each having a mean chain length p of 8, or a mixture of the specified compounds.
9. A catalyst as claimed in claim 1, wherein the compound of the formula (2) is octadecyltrimethylammonium chloride, distearyldi-methylammonium chloride, tetramethyl-ammonium chloride, tetramethylammonium bromide, hexadecyltrimethylammonium chloride, benzyltrimethylammonium chloride, hexadecyl-tributylphosphonium bromide, stearyl tributylphosphonium bromide, tetrabutylphosphonium chloride, tetrabutyl-phosphonium bromide or tetraoctylphosphonium bromide.
10. A catalyst as claimed in claim 1, wherein the component c) is a mixture of polyethylene glycol dimethyl ethers and has a mean molecular mass of 500.

* * * * *